United States Patent [19]
Tadir et al.

[11] Patent Number: 5,478,339
[45] Date of Patent: Dec. 26, 1995

[54] INTRAUTERINE DEVICE FOR LASER LIGHT DIFFUSION AND METHOD OF USING THE SAME

[75] Inventors: Yona Tadir, Irvine; Michael W. Berns, Trabuco Canyon, both of Calif.; Lars O. Svaasand, Trondheim, Norway; Bruce J. Tromberg, Irvine, Calif.

[73] Assignee: The Regents of the University of California, Oakland, Calif.

[21] Appl. No.: 297,752

[22] Filed: Aug. 30, 1994

[51] Int. Cl.⁶ ................................................. A61B 17/36
[52] U.S. Cl. .................... 606/15; 606/16; 607/95; 604/281
[58] Field of Search .................... 606/7, 15, 16, 606/17; 607/95; 604/281

[56] References Cited

U.S. PATENT DOCUMENTS 4,998,930  3/1991  Lundahl ................................ 606/15
5,298,026  3/1994  Chang .................................. 606/15

Primary Examiner—Stephen C. Pellegrino
Assistant Examiner—Sonya Harris-Ogugua
Attorney, Agent, or Firm—Daniel L. Dawes

[57] ABSTRACT

An improved device for delivery of photoenergy from a light source, such as a laser, into a uterine cavity for photodynamic therapy is comprised of a plurality of optic fibers, which are bundled together and inserted into the uterine cavity by means of a uterine cannula. The cannula is positioned within the uterine cavity at a preferred location and then withdrawn thereby allowing the plurality of optic fibers to splay or diverge one from the other within the cavity. Different portions of the distal tip of the optic fiber is provided with a light diffusing tip, the remainder being provided with a nondiffusing tip portion. The fiber optic shape, as well as the segment which is permitted to actively diffuse light through the tip, is selected in order to provide a more uniform exposure intensity of the photo energy or at least sufficient radiation directed to each segment of the uterine walls.

14 Claims, 2 Drawing Sheets

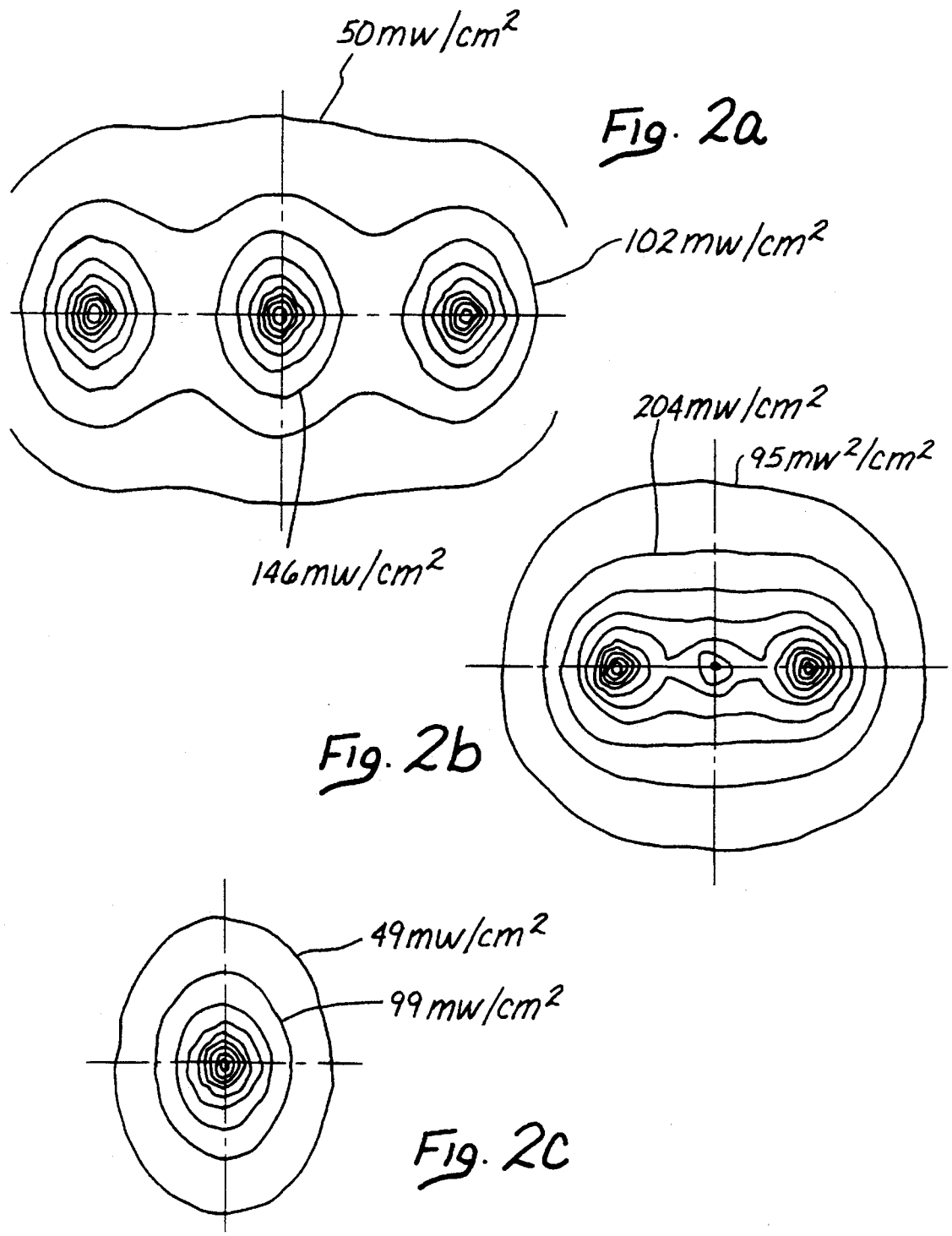

INTRAUTERINE DEVICE FOR LASER LIGHT DIFFUSION AND METHOD OF USING THE SAME

This invention was made with Government support under Grant No. CA-32248, awarded by the National Institute of Health, Contract No. N00014-91-C-0134, awarded by the Office of Naval Research and Contract No. DE-FG03-91-ER61227, awarded by the Department of Energy. The Government has certain rights in this invention.

BACKGROUND OF THE INVENTION

1. Field of the Invention

The invention relates to the field of photodynamic therapy, and in particular to devices and methods used for intrauterine photodynamic exposures.

2. Description of the Prior Art

Intrauterine light exposures for photodynamic therapy require exposure of drug impregnated tissue with a light intensity about an active threshold intensity and/or dosage. Given the large inner surface area of the uterine cavity the problem is to provide a delivery device which can provide an activating exposure to this area without leaving any portion of the inner surface unexposed or underexposed.

Grace et al., "Two-Piece Tip for Fiber Optic Catheter," U.S. Pat. No. 5,263,952 (1993), assigned to Spectranetics of Colorado Springs, Colo., shows a two-piece tip for a fiber optic catheter. The catheter provides for a more uniform illumination using a two-piece tip. The ends of the optical fibers do not extend parallel to the catheter axis, and in fact, the ends of the optical fibers may have exit surfaces which are perpendicular to the axis of the catheter. Alternatively, the ends of the optical fibers may have exit surfaces at an angle from the perpendicular. Referring specifically to FIG. 1, a light conveying cable 16 is terminated by a tip 28. Two-piece 28 is shown in FIG. 2 that is comprised of optical fibers 208 disposed to form an outer lumen 220 and an inner lumen 222. Thus, the light diffusing tip provides for a more uniform distribution of energy for photodynamic treatment.

Additional embodiments of the two-piece tip are shown in FIGS. 3–6. Grace simply shows a hollow cylindrical bundle of optic fibers disposed in a catheter and terminated between distal end clamping rings 204 and 206 in FIG. 2. The exit areas of the optic fibers may be perpendicular to the axis of the catheter as shown in FIG. 2, or angled in some manner as shown in the embodiments of FIGS. 3–6. The embodiments of FIGS. 4 and 5 show a angling of the optic fiber bundles that can be broadly considered as a Y form of divergence.

Grace fails to show a fiber array which is capable of springing outwardly in a body or uterine cavity to provide optimal illumination of the cavity or uterine walls.

Baker et al., "Optical Fiber Diffusion Tip for Uniform Illumination," U.S. Pat. No. 5,207,669 (1993), assigned to C. R. Bard, Inc. of Murray Hill, N.J., shows a laser balloon catheter assembly 12 in FIG. 1 which includes an optical fiber tip assembly 24 shown in greater detail in FIG. 2. Optical fiber 32 extends from connector 20 which is connected to an output of a laser source. Optical fiber 32 extends through flexible tube 10 and terminates in an optical fiber tip 24. Optical fiber tip assembly 24 is used to direct laser energy outwardly with the desired radiation pattern. Tip assembly 24, as seen in FIGS. 3 and 4, includes an extension of core 44, a thin cladding 48 and jacket 50. The characteristics of cladding 48, core 44 and jacket 50 are such as to provide uniform cylindrical diffusion or other desired pattern of radiation over the length of the entire diffusion tip 24. Baker has only a single catheter body and no means is provided for diverging diffusion segments.

Lundahl, "Intracavity Laser Phototherapy Method," U.S. Pat. No. 4,998,930 (1991), assigned to Phototherapeutic Systems, Martinez, Calif., describes a method of laser phototherapy using uniform irradiation of the inner walls of a hollow organ. The uniform distribution of energy is made possible by an optical laser fiber with isotropic diffuser tip. Diffuser tip 28 is located at the upper light output end of a light conducting fiber 27 best depicted in FIG. 2. Lundahl only shows a single irradiating diffusion segment.

Khoury, "Laser Catheter Diffuser," U.S. Pat. No. 5,151,096 (1992), assigned to Angiolaz, Inc. of Rockingham, Vt., shows the use of a laser catheter diffuser for activating photodynamic therapy in soft cancerous tissues. The diffuser includes an unclad fiber optic core with a reflective cap at a terminal end of the core. The reflective cap 14 is fixed to terminal end 20 of unclad fiber optic core 12 as shown in FIG. 2. The tip is surrounded by a diffuser matrix 16 with a pointed end 42 forming a collar 44 around an exterior edge 46 of reflective cap 14. In practice, the laser light travels along the laser catheter and is reflected from side to side within fiber optic core by cladding layer surrounding the core. Most of the light passes out of the core and diffuses away from the core through the diffuser matrix. The light that remains within the core reaches its terminal end and is reflected back by the reflective cap to diffuse out of the core via the diffuser matrix. By the means, a more uniform distribution of energy and a photodynamic therapy process is achieved. Khoury fails to show a branched fiber optic termination as the mechanism for light distribution in the photodynamic therapeutic application.

Narciso, Jr., "Laser Delivery System," U.S. Pat. No. 5,169,395 (1992), assigned to PDT Cardiovascular, Inc. of Goleta, Calif., shows another application of a catheter tip for delivering laser light for photodynamic therapy in combination with photoreactive molecules.

McCaughan, Jr., "Apparatus for Producing a Spherical Pattern of Light and Method of Manufacture," U.S. Pat. No. 4,693,556 (1987), assigned to Laser Therapeutics, Inc. of Worthington, Ohio, describes an apparatus for producing a spherical pattern of light in a radiating tip. As best shown in FIG. 2, the operation depends upon a scattering region 7 which is large in comparison to the source of light 6. Thus, when light emerges from the core of optic fiber 6, it encounters a strong scattering region 7. The light is repeatedly scattered in region 7 to give a uniform spherical pattern of radiation.

Means for diffusing the laser light delivered through the end of the catheter is well known. Radiation of body cavities by laser diffusers is also well known. Angled fiber optics and diffusing segments for fiber optics ends in catheters are generally described.

What is needed is some type of device or method for delivering light to the inner surface of a body cavity, such as the uterus, which will provide sufficient dosage and/or intensity of light to the entire inner surface of the cavity.

BRIEF SUMMARY OF THE INVENTION

The invention is a device for use with a source of light for providing photodynamic treatment to the walls of a body cavity. The device comprises a plurality of optic fibers for transmitting photoenergy from the source of light to the body cavity, and a cannula for temporarily combining the plurality of optic fibers into a bundle for insertion into the body cavity. The optic fibers are arranged and configured to diverge from each other when the cannula is at least partially withdrawn from that portion of the optic fibers inserted into the body cavity. The optic fibers emit photoenergy along at least a portion of their length disposed into the body cavity. As a result, an exposure of photoenergy is provided to the walls of the body cavity at and above a predetermined minimum threshold intensity.

Each of the plurality of optic fibers has a light diffusing tip of differing operative length. The differing operative lengths are distributed among the plurality of optic fibers to provide a more even level of intensity of illumination in the body cavity. The operative lengths are chosen to provide a more even or at least complete exposure in inserted into a body cavity like the uterus having a funnel-shape, and when the plurality of optic fibers are inserted into the body cavity through an apex of the funnel shaped cavity.

At least a portion of one of the plurality of optic fibers has a curved end to provide photodynamic exposure of a wall of the body cavity obliquely inclined with respect to the plurality of optic fibers, namely the fundus of the uterus.

Each of the plurality of optic fibers are bound into a single bundle except for their tips which are inserted into the body cavity. The tips diverge one from the other after the cannula is removed by means of inherent resiliency within the optic fibers. Alternatively, the device further comprises an element for urging the plurality of tips into a predetermined splayed pattern.

The invention is also an improvement in a method of exposing drug-treated intrauterine walls by photodynamic therapy comprising the steps of inserting a cannula into the uterine cavity. The cannula carries a plurality of optic fibers completely disposed within the cannula. The cannula is positioned within the uterine cavity into a predetermined location. The cannula is withdrawn from the uterine cavity while leaving the plurality of optic fibers disposed therein. The optic fibers are splayed while in the uterine cavity to provide full exposure of the intrauterine walls. Photoenergy is applied through the plurality of optic fibers to diffuse it from that portion of the optic fibers inserted in the uterine cavity and to expose the treated intrauterine walls with an activating level of photoenergy. As a result, substantially complete irradiation of the intrauterine walls is achieved.

The step of withdrawing the cannula exposes different light emitting lengths of the plurality of optic fibers for irradiation of the intrauterine walls. The step of withdrawing the cannula allows the fiber optics to be splayed within the uterine cavity into a preferred configuration.

Finally, the invention can also be characterized as an intrauterine apparatus for photodynamic therapy comprising a source of photoenergy and a plurality of optic fibers coupled to the source of photoenergy for transmitting the photoenergy from the source through the optic fibers. A cannula is provided for bundling and inserting the plurality of optic fibers into a uterine cavity having uterine walls. A diffusing tip is provided on each one of the plurality of optic fibers for diffusing the photoenergy along a predetermined surface on each of the diffusing tips. As a result, substantially all of the intrauterine walls are irradiated by the apparatus at a level sufficient to provide effective photodynamic therapy.

The invention may be better visualized by now turning to the following drawings wherein like elements are referenced by like numerals.

BRIEF DESCRIPTION OF THE DRAWINGS

FIG. 2a is a cross sectional view of the effective treatment area of the uterus at a level 2a—2a of FIG. 1.

FIG. 2b is a diagrammatic depiction of the light distribution of the effective treatment area of the uterus at a level 2b—2b of FIG. 1.

FIG. 2c is a diagrammatic depiction of the light distribution of the effective treatment area of the uterus at level 2c—2c of FIG. 1.

The invention and its various embodiments may now be better understood by turning to the following detailed description.

DETAILED DESCRIPTION OF THE PREFERRED EMBODIMENTS

Photodynamic therapy for the diagnosis and treatment of uterine abnormalities has recently been developed with promising results. The light diffusing device of the invention provides for full uterine cavity illumination to provide exposure with minimum pain and trauma to the patient. The catheter is characterized in part by diverging fiber optic bundles at the end of the catheter tip. The diverging optical fibers are deployed after insertion into a body cavity and provide for diffusive laser illumination along the splayed tip segments. The catheter has laser-diffusive segments which are inserted into a body cavity within a cannula and then allowed to widely diverge to provide uniform cavity irradiation when the cannula is removed from the cavity.

An improved device for delivery of photoenergy from a light source, such as a laser, into a uterine cavity for photodynamic therapy is comprised of a plurality of optic fibers, which are bundled together and inserted into the uterine cavity by means of a uterine cannula. The cannula is positioned within the uterine cavity at a preferred location and then withdrawn thereby allowing the plurality of optic fibers to splay or diverge one from the other within the cavity. Different portions of the distal tip of the optic fiber is provided with a light diffusing tip, the remainder being provided with a nondiffusing tip portion. The fiber optic shape, as well as the segment which is permitted to actively diffuse light through the tip, is selected in order to provide a more uniform exposure intensity of the photo energy or at least sufficient radiation directed to each segment of the uterine walls.

Figure 1:
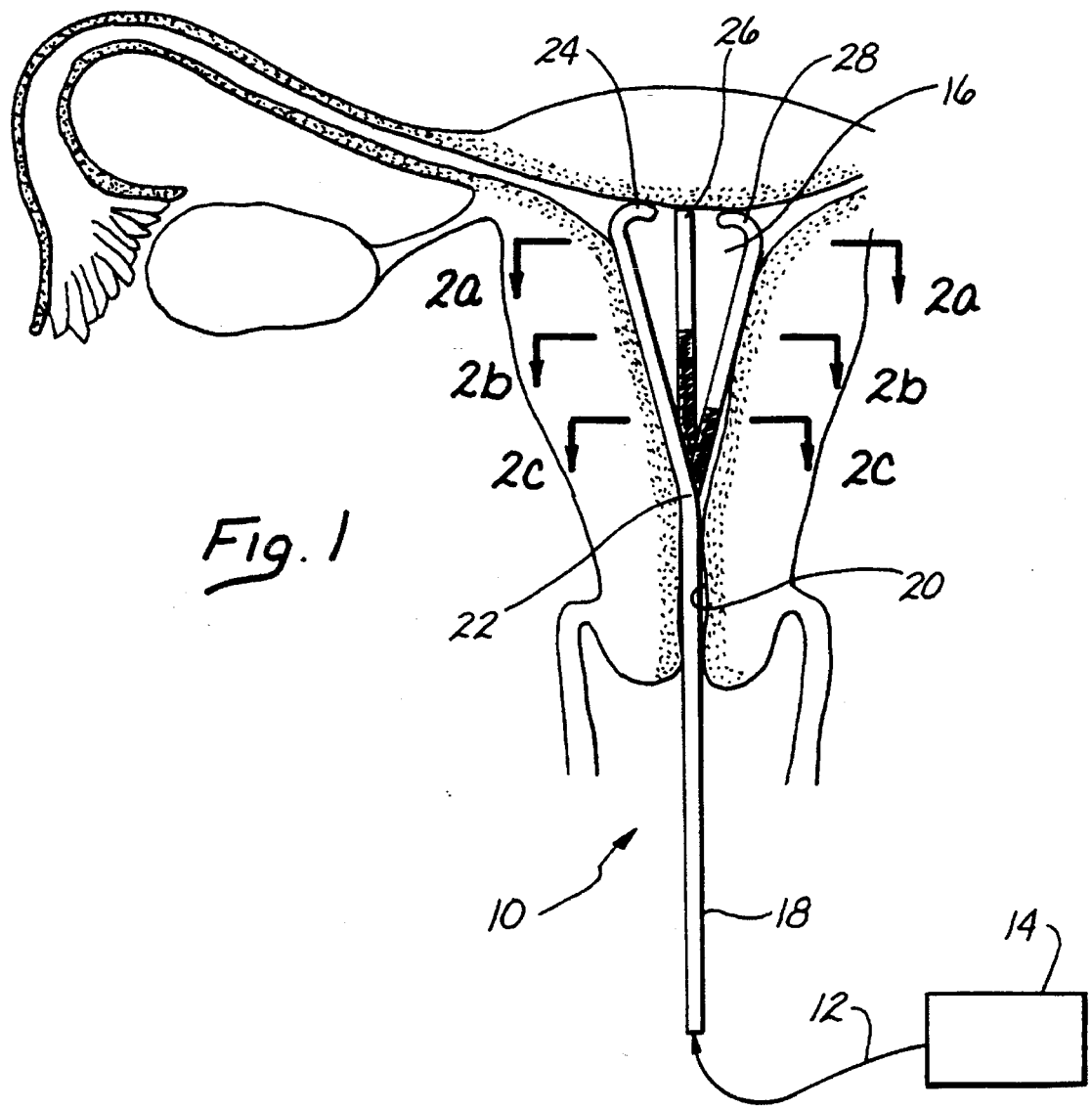
FIG. 1 is a diagrammatic depiction of the human uterus, fallopian tube and ovary, showing the device of the invention inserted for purposes of uterine wall exposure.

As seen in the simplified diagrammatic depiction of FIG. 1, the uterine exposure device 10 is comprised of a bundle 12 of a plurality of optical fibers coupled at their proximal end to a conventional laser-light source 14. The distal end of the bundle is inserted into the uterine cavity 16 by conventional means, such as by using an insertion cannula 18 in which fiber bundle 12 is slidingly disposed. Cannula 18 is then inserted through the cervical canal 20 and carefully advanced until the uterine fundus is felt. Cannula 18 is then withdrawn to at least the position where its distal tip 22 is at the base of uterine cavity 16 allowing deployment of the plurality of optical fibers within bundle 12.

In the illustrated embodiment, three such optical fibers 24, 26 and 28 are depicted in FIG. 1. It is entirely within the scope of the present invention, however, that the number of optical fibers may vary anywhere from a single fiber to a large multiplicity, consistent with the teaching of the present invention. As a practical matter, it is expected that two to six separate optical fibers will usually be sufficient to provide the needed exposure levels.

Figure 3:
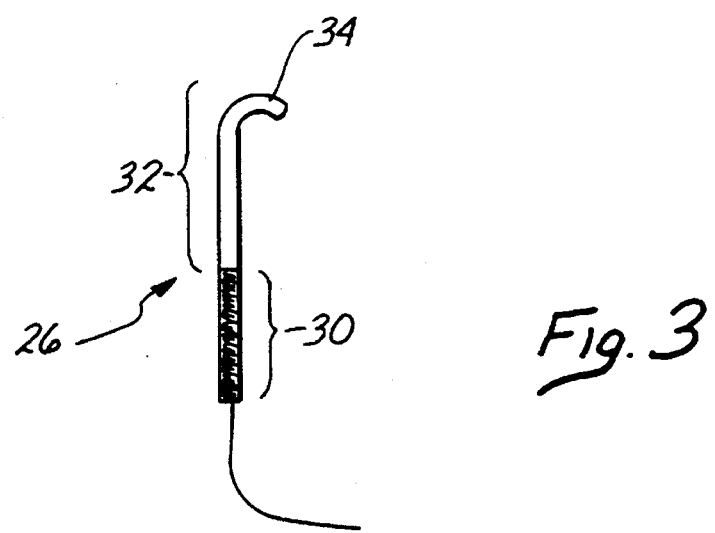
FIG. 3 is a simplified side elevational view of one of the three diffusing tips shown in the embodiment of FIG. 1.

FIG. 3 is a simplified side elevational view of one of the optical fibers 26 included within bundle 12. By means well known to the art, the optical fibers may be comprised of a nondiffusing portion 30 and a diffusing portion 32. The laser light delivered from source 14 through the optical fiber into the diffusing tip is not admitted from nondiffusing portion 30, but only from the diffusing portion 32. In general, diffusion of the laser light from the diffusing portion is approximately equally distributed in all directions along the exposed surface of diffusing portion 32.

In the illustrated embodiment, diffusing portion 32 is shown with a biased or curved end 34 which provides a means of directing laser light to the top of the uterine cavity 16 as well as to its sides. Other means may be provided for exposure of the top wall of the uterus such as diffusing tip end lenses and the like.

The light diffusion pattern from the plurality of diffusing tips 24–28 shown in FIG. 1 is better depicted in the diagrammatic view of FIGS. 2a–2c. As shown in FIG. 2a, which shows the light distribution at the level of section 2a—2a of FIG. 1, diffusing tips 24, 26 and 28 are each exposed and emitting light across the entire section width of uterine cavity 16, providing a therapeutically effective intensity within light halos 34. Only diffusing tips 24 and 28 are exposed at section 2b—2b of FIG. 1 as shown in the diagrammatic depiction of FIG. 2b. Uterine cavity 16 is generally in the shape of a flattened funnel so that the surface area of the cavity walls decreases as the cervical canal is approached and a smaller area of effective photodynamic exposure levels is required. In addition, three diffusing tips which are splayed more or less flatly on a plane are capable of providing a light coverage sufficient to expose all surface areas of the cavity 16 with an effective light dose in one exposure session. Fibers 24–28 may splay or diverge generally in the plane of the flatten funnel shaped uterine cavity 16, may be prebiased to assumed the needed splayed positions, or may incorporate a spacer, form or internal contour defined in or near tip 22 of cannula 18 to urge fibers 24–28 into the desired splayed pattern.

At the very lowest level, as shown in FIG. 2c, taken through section lines 2c—2c of FIG. 1, only diffusing tip 24 is exposed thereby providing the smallest area of photodynamic exposure at the narrowed base and entry into uterine cavity 16. Spreading of the uterine walls by 3–5 mm with a conventional fluidic distending medium caused a 5 to 10 fold increase in the penetration of light into the endometrium and myometrium.

The catheter exposure device of FIG. 1 is used in the method of the invention to cause selective destruction of human endometrium by photodynamic therapy. Photodynamic therapy is a technique that destroys tissue through interaction between absorbed laser light and a retained photosynthesizer. The process involves intravenous or topical administration of a photosensitive drug which is retained in the target tissue. When light of sufficient energy and appropriate wavelength interacts with the synthesizer, a highly reactive oxygen intermediate is generated. These intermediates, which are primarily singlet molecular oxygen, irreversibly oxidize the essential cellular components of the tissue. The resulting photodestruction of crucial organelles ultimately causes tissue necrosis.

In the illustrated embodiment, for example, 5-aminolevulinic acid is used as a photosynthesizer because it offers several advantages of selective endometrial destruction following topical and systematic application. Topical application of photosynthesizer inherently involves a higher local drug intake and the requirement that there be no or little systematic adverse reactions such as skin photosensitivity. 5-aminolevulinic acid is a naturally occurring substance found in humans as a part of the normal metabolic processes necessary for life.

The administration of the photosynthesizer, the first committed intermediate in the heme biosynthesis pathway, results in the production of porphyrin precursors, particularly protoporphyrin iX(PpiX) which is a potent photosynthesizer. Recent studies of the use of 5-aminolevulinic acid for endometrial ablation have demonstrated selective conversion into PpiX and retention of this compound by the endometrium.

5-aminolevulinic acid solutions at concentrations greater than 40 milligrams per milliliter are highly acidic, whereas the pH of normal uterine fluid in humans during various phases of the menstrual cycle range from a pH of 5.9 to 7.3. In the illustrated embodiment, titration pH 6.0 was chosen since 5-aminolevulinic acid solution manufactured under the trademark, HYSKON™, adjusted to a pH of greater than 6.0 leads to turbidity. 5-aminolevulinic acid in DEXTRAN 70™ manufactured by Pharmacia, Inc. of Piscataway, N.J., was used because of the high viscosity of the solution which minimized spillage through the fallopian tubes into the abdominal cavity. The HYSKON™ solution is a viscous, hydrophyllic, branched polysaccharide which is routinely used for uterine distension during hysteroscopy.

Four hundred milligrams of 5-aminolevulinic acid as manufactured by DUSA Pharmaceuticals, Inc. of Denville, N.J., were used in DEXTRON 70™. The crystallized 5-aminolevulinic acid hydrochloride which is dissolved in the HYSKON™ solution up to the concentration of 400 milligrams per milliliter was titrated with 10N sodium hydroxide to a pH of 6 extemporaneously just before use under sterile conditions.

Topical application of the solution was performed in a lithotomy position.R Standard bivalve speculum was then inserted and the cervix cleaned with povidone-iodine. A cervical cannula manufactured by C. R. Bard, Inc. of Billerica, Mass., with an outer diameter of 4 millimeters was then inserted into the cervical canal up to the plastic stop. About 1 to 2 milliliters of 400 milligram per milliliter solution of 5-aminolevulinic acid in HYSKON™ was slowly ejected into the uterine cavity. The time span for injection is approximately 30 seconds and accomplished at a uniform flow rate through a slow manual push.

At various time intervals, following the drug application, such as 1, 3 and 6 hours later, the intrauterine light device of FIGS. 1–3 was inserted into uterine cavity in a manner similar to the insertion of a contraceptive IUD. The fibers were then connected to a light source emitting laser light or other appropriate photoenergy to provide levels of intensities sufficient to induce photochemical changes in the topically applied solution.

In the above example, laser light with a wavelength at approximately 630 nm was chosen with a single exposure at about 400 milliwatts per centimeter$^2$ for 600 seconds. Each diffusing tip 24, 26 and 28 received approximately identical amounts of photoenergy per active diffusing fiber optic tip from source 14. Clearly, the photoenergy delivered through each corresponding optic fiber within bundle 12 to diffusing tips 24, 26 and 28 are delivered through the respective diffusing tips over their corresponding differing areas. For example, the effective radiating length and surface area of diffusing tip 24 are 3 cm and 0.75 cm$^2$ respectively; 1.5 cm and 0.38 cm$^2$ respectively for diffusing tip 26; and 2.25 cm and 0.57 cm$^2$ respectively for tip 28. Therefore, notwithstanding that the delivered light intensities at a given distance from each of tips 24, 26 and 28 may vary, intensity variations due to the tip-to-tissue distance, which varies as the inverse square law, more than exceeds the differences in surface photointensity on diffusing tips 24–28.

Further, the photodynamic therapeutic effect is a threshold effect which is activated as long as the light exposure exceeds a threshold minimum. Therefore, within reason, in order to provide effective exposure to the uterine walls, it is only necessary that the light intensities at the target levels exceed the minimum threshold intensity level. It is not a requirement that the photoexposure levels be uniform, provided they exceed the minimum threshold. It has been found in practice that the splayed multifiber diffusing tips of uterine device 10 is sufficient to achieve this result.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following claims. The following claims are, therefore, to be read to include not only the combination of elements which are literally set forth, but all equivalent elements for performing substantially the same function in substantially the same way to obtain substantially the same result. The claims are thus to be understood to include what is specifically illustrated and described above, what is conceptionally equivalent, and also what essentially incorporates the essential idea of the invention.

We claim:

1. A device for use with a source of light for providing photodynamic treatment to walls of a body cavity comprising:

a plurality of optic fibers for transmitting photoenergy from said source of light to said body cavity; and a cannula for temporarily combining said plurality of optic fibers into a compact configuration for insertion into said body cavity;

wherein said optic fibers are arranged and configured to diverge from each other when said cannula is at least partially withdrawn from that portion of said optic fibers inserted into said body cavity, said optic fibers emitting photoenergy along at least a portion of their length disposed into said body cavity, wherein each of said plurality of optic fibers has a light diffusing tip and wherein each of said diffusing tips has an active portion through which light is diffused, at least two of said diffusing tips having differently sized active portions which are disposed at predetermined and distinct locations within said cavity when said optic fibers are deployed for irradiation, whereby an exposure of photoenergy is provided to said walls of said body cavity at and above a predetermined minimum threshold intensity.

2. The device of claim 1 said differing operative lengths of said diffusing tips being distributed among said plurality of optic fibers to provide a more even level of intensity of illumination in said body cavity when said body cavity has a funnel-shape and said plurality of optic fibers are inserted into said body cavity through an apex of said funnel shaped cavity.

3. The device of claim 1 wherein at least a portion of one of said plurality of optic fibers has a curved end to provide photodynamic exposure of a wall of said body cavity obliquely inclined with respect to said plurality of optic fibers.

4. The device of claim 3 said differing operative lengths of said diffusing tips being distributed among said plurality of optic fibers to provide a more even level of intensity of illumination in said body cavity when said body cavity has a funnel-shape and said plurality of optic fibers are inserted into said body cavity through an apex of said funnel shaped cavity.

5. An improvement in a method of exposing drug-treated intrauterine walls by photodynamic therapy comprising the steps of:

inserting a cannula into an uterine cavity defined by said intrauterine walls, said cannula carrying a plurality of optic fibers completely disposed within said cannula;

positioning said cannula within said uterine cavity into a predetermined location;

withdrawing said cannula from said uterine cavity while leaving said plurality of optic fibers disposed therein;

splaying said optic fibers while in said uterine cavity to provide full exposure of said intrauterine walls; and applying photoenergy through said plurality of optic fibers to diffuse said photoenergy from that portion of said optic fibers inserted in said uterine cavity to expose said treated intrauterine walls with activating photoenergy, whereby substantially complete irradiation of said intrauterine walls is achieved.

6. The improvement of claim 5 where said step of withdrawing said cannula exposes different light emitting lengths of said plurality of optic fibers for irradiation of said intrauterine walls.

7. The improvement of claim 6 where said step of withdrawing said cannula allows said fiber optics to be splayed within said uterine cavity into a preferred configuration.

8. The improvement of claim 5 where said step of withdrawing said cannula allows said fiber optics to be splayed within said uterine cavity into a preferred configuration.

9. An intrauterine apparatus for photodynamic therapy of a normally configured uterine cavity comprising:

a source of photoenergy at a substantially nonhyperthermic energy level;

a plurality of optic fibers coupled to said source of photoenergy for transmitting said photoenergy from said source through said optic fibers;

a cannula for bundling and inserting said plurality of optic fibers into a uterine cavity having uterine walls; and a diffusing tip provided on each one of said plurality of optic fibers for diffusing said photoenergy along a predetermined surface length of each of said diffusing tips, said optic fibers, said optic fibers having means for splaying said optic fibers in a plane defined between said walls of said uterine cavity when said cavity is in a normally collapsed configuration and providing contact photo-illumination of said walls of said uterine cavity, wherein said optic fibers splayed in a plane of the uterine cavity to assume a flattened funnel shape of said cavity whereby substantially all of said intrauterine walls are irradiated by said apparatus at a level sufficient to provide effective photodynamic therapy.

10. The apparatus of claim 9 wherein at least one of said optic fibers has a substantially curved distal diffusing tip to provide irradiation along an axis oblique to said primary axis of said optic fiber within said uterine cavity.

11. The apparatus of claim 9 wherein said plurality of optic fibers comprise three optic fibers each having a differing active region for emitting photoenergy, said active region on each of said fibers being progressively lengthened from said distal tip of each said optic fiber.

12. An intrauterine apparatus for photodynamic therapy comprising:

a source of photoenergy;

a plurality of optic fibers coupled to said source of photoenergy for transmitting said photoenergy from said source through said optic fibers;

a cannula for bundling and inserting said plurality of optic fibers into a uterine cavity having uterine walls; and a diffusing tip provided on each one of said plurality of optic fibers for diffusing said photoenergy along a predetermined surface on each of said diffusing tips, wherein each of said diffusing tips has an active portion through which light is diffused, at least two of said diffusing tips having differently sized active portions which are disposed at predetermined and distinct locations within said uterine cavity when said optic fibers are deployed for irradiation, whereby substantially all of said intrauterine walls are irradiated by said apparatus at a level sufficient to provide effective photodynamic therapy.

13. The apparatus of claim 12 wherein said active portion of each of said diffusing tip comprises a distal end portion of each of said optic fibers, said end portions of said optic fibers, which have a differing active portion, being of differing length from said distal end of said optic fiber.

14. The apparatus of claim 12 wherein at least one of said optic fibers has a substantially curved distal tip to provide irradiation along an axis oblique to said primary axis of said optic fiber within said uterine cavity.

* * * * *